United States Patent [19]

Hoshi et al.

[11] Patent Number: 5,380,490
[45] Date of Patent: Jan. 10, 1995

[54] APPARATUS FOR MEASURING A TEST SPECIMEN

[75] Inventors: Hiroaki Hoshi, Yokohama; Matsuomi Nishimura, Ohmiya; Kazumi Tanaka, Yokohama; Takeshi Miyazaki, Ebina; Toshikazu Ohnishi, Machida; Hidehito Takayama, Chigasaki, all of Japan

[73] Assignee: Canon Kabushiki Kaisha, Tokyo, Japan

[21] Appl. No.: 821,049

[22] Filed: Jan. 16, 1992

[30] Foreign Application Priority Data

Jan. 18, 1991 [JP] Japan .................. 3-019551
Dec. 6, 1991 [JP] Japan .................. 3-349154
Jan. 8, 1992 [JP] Japan .................. 4-020416

[51] Int. Cl.[6] ............................. G01N 33/543
[52] U.S. Cl. ............................ 422/73; 422/55; 422/68.1; 422/76; 422/82.01; 204/400; 204/403; 324/692; 324/693; 324/724
[58] Field of Search .............. 422/55, 68.1, 73, 76, 422/82.01, 82.02; 324/692, 693, 724; 204/400, 403

[56] References Cited

U.S. PATENT DOCUMENTS

| | | | |
|---|---|---|---|
| 3,635,681 | 1/1972 | Rogers | 422/82.02 |
| 3,714,562 | 1/1973 | McNerney | 324/724 |
| 4,398,894 | 8/1983 | Yamamoto | 422/73 |
| 4,436,827 | 3/1984 | Tamagawa | 436/534 |
| 4,446,239 | 5/1984 | Tsuji et al. | 436/532 |
| 4,447,396 | 5/1984 | Kano | 422/73 |
| 4,452,759 | 6/1984 | Takekawa | 422/73 |
| 4,596,695 | 6/1986 | Cottingham | 422/58 |
| 4,999,582 | 3/1991 | Parks et al. | 324/438 |
| 5,001,053 | 3/1991 | Takahashi et al. | 435/7.1 |
| 5,059,395 | 10/1991 | Brittenham et al. | 422/73 |
| 5,066,372 | 11/1991 | Weetall | 204/153.1 |
| 5,093,268 | 3/1992 | Leventis et al. | 436/172 |
| 5,141,868 | 8/1992 | Shanks et al. | 435/288 |

FOREIGN PATENT DOCUMENTS

| | | |
|---|---|---|
| 0079717 | 5/1983 | European Pat. Off. . |
| 0177988 | 9/1984 | European Pat. Off. . |
| 0170375 | 2/1986 | European Pat. Off. . |
| 0246846 | 11/1987 | European Pat. Off. . |
| 0261868 | 3/1988 | European Pat. Off. . |
| 0336013 | 10/1989 | European Pat. Off. ......... 422/82.01 |
| 0479231 | 4/1992 | European Pat. Off. . |

*Primary Examiner*—James C. Housel
*Assistant Examiner*—Harold Y. Pyon
*Attorney, Agent, or Firm*—Fitzpatrick, Cella, Harper & Scinto

[57] ABSTRACT

An apparatus is so constructed as to measure a specific substance in a test specimen by the degree of the aggregation of carrier particles in a reaction solution in which the test specimen is mixed with the carrier particles which carry a substance specifically binding to the specific substance. The apparatus includes a substrate having comb-shaped electrodes mounting the reaction solution and amplifier and alternating oscillator for displaying a variable voltage to the comb-shaped electrodes. The test specimen measuring apparatus having the structure accelerates the aggregation of the reaction solution by applying an alternating voltate to the comb-shaped electrodes in a state that the reaction solution is being mounted on the substrate, and detects the spatial spectrum of the comb-shaped electrodes on which the reaction solution is mounted, thus performing the qualitative or quantitative detection of the presence of the substance in the test specimen.

5 Claims, 9 Drawing Sheets

APPARATUS FOR MEASURING A TEST SPECIMEN

BACKGROUND OF THE INVENTION

1. Field of the Invention

The present invention relates to the field of measurement of a test specimen for detecting a substance in the test specimen qualitatively or quantitatively.

2. Related Background Art

As a method for detecting in a test specimen so-called immunoactive substance such as an antigen or an antibody which is specifically bound to a specified antibody or antigen, there is known a method in which the immunoactive substance is sensitized to carrier particles (latex particles, glass particles, ceramic particles, kaolin, carbon black, colloidal particles such as erthrocytes and other animal blood components, and the like), and the carrier particles are reacted with a test specimen in a liquid medium, and the aggregating state of the carrier particles in the reaction solution is observed and verified with the naked eye, thereby detecting qualitatively the substance which is specifically bound to the sensitized substance. Also, for a quantitative detection, there is known a method in which an immunoactive substance is detected quantitatively in such a manner that the reaction solution is injected into a transparent test container and white light or the like is radiated thereto to measure the intensity fluctuations of the transmitting light, the scattering rays of light, and others.

However, with the above-mentioned conventional methods, it is difficult to maintain reproducibility while making the aggregating conditions constant. Moreover, when the aggregating state is determined with the naked eye, the detection tends to lack its quantitativeness. As a result, the test results are less accurate and reliable. Also, since a mechanical vibration should be given to the reaction solution in order to accelerate its aggregation, the mechanism of apparatus becomes large and complicated. In addition, although the method for performing a quantitative detection through the measurement of the transmitting light, scattered light and the like contributes to an improved quantitative accuracy, there is a problem that it takes a longer time to complete the test because the aggregating state must be measured twice or more after the reaction.

SUMMARY OF THE INVENTION

It is an object of the present invention to provide an apparatus and method for measuring a test specimen capable of performing a highly accurate qualitative or quantitative detection of a substance in the test specimen with a simple structure in a short period of time.

DETAILED DESCRIPTION OF THE PREFERRED EMBODIMENTS

Hereinafter, the present invention will be described in detail in conjunction with the accompanying drawings.

Figure 1:
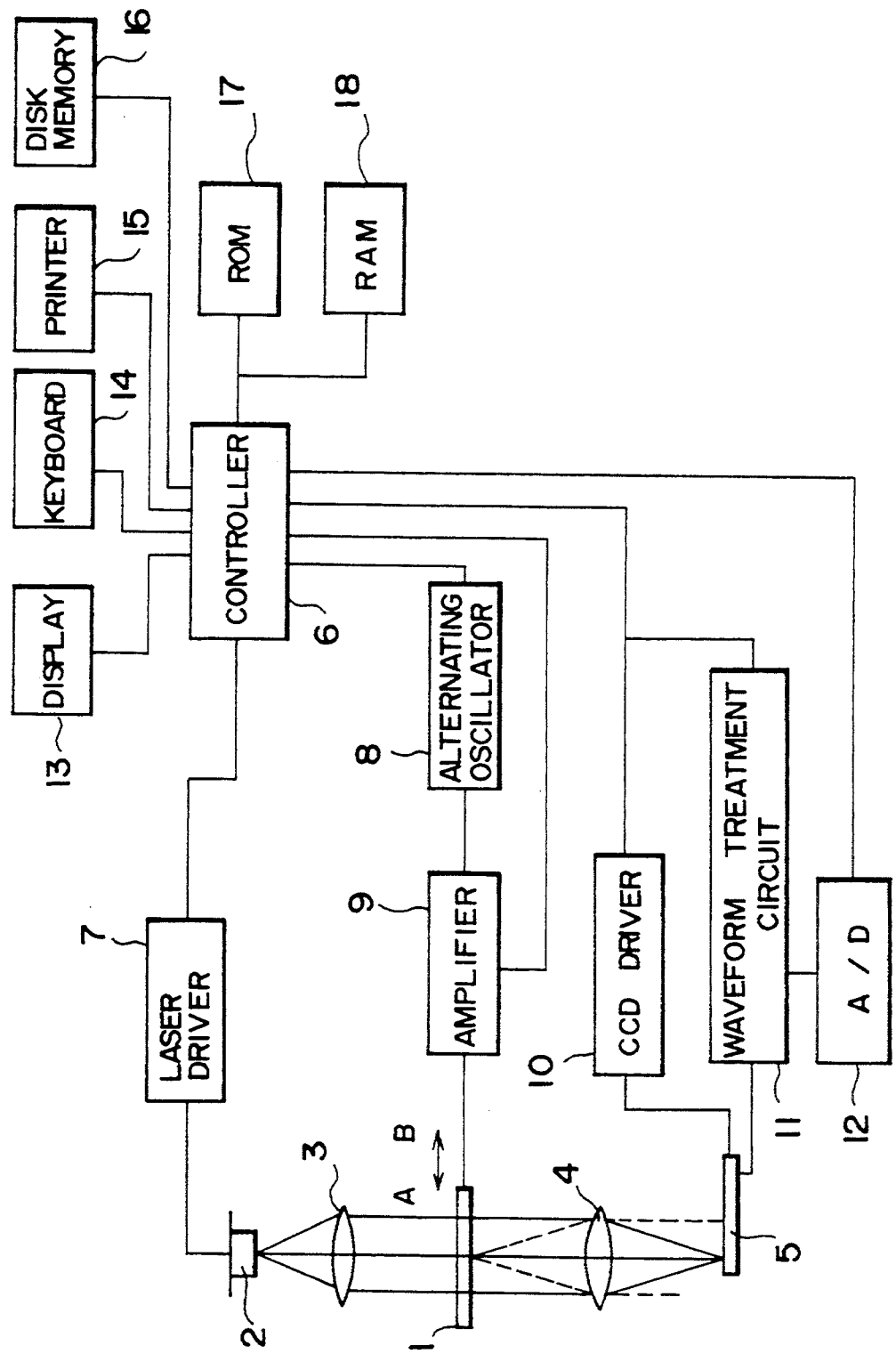
FIG. 1 is a diagram showing the structure of a first embodiment according to the present invention.

FIG. 1 is a diagram showing the structure of a first embodiment according to the present invention. In FIG. 1, a reference numeral 1 designates a sample plate for mounting the carrier particles which carry an immunoactive substance such as a monoclonal antibody on opaque insoluble fine particles, and the reaction solution in which an objective substance to be detected is reacted in a liquid medium. A semiconductor laser light source 2 and collimator lens 3 are provided on the optical axis to face the sample plate 1 which is horizontally arranged. A lens 4 and a photoelectric element 5 such as the primary CCD are arranged on the optical axis behind the sample plate 1 to receive the light beam transmitted through the sample plate 1. The sample plate 1 is adjusted to match the front side focusing plane of the lens 4, and the photoelectric element 5 is adjusted to match the rear side focusing plane of the lens.

Figure 2:
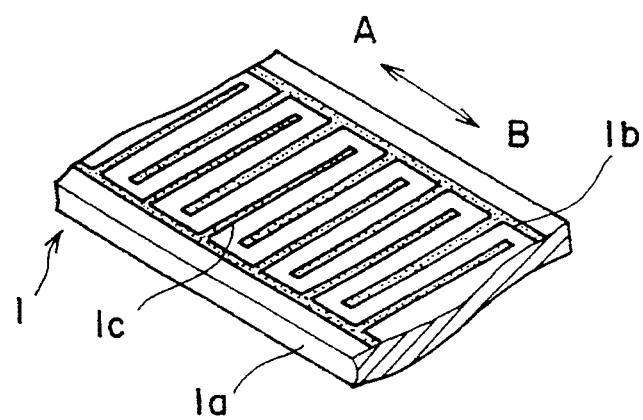
FIG. 2 is a perspective view illustrating a sample plate.

FIG. 2 is a perspective view illustrating the sample plate 1. The sample plate 1 is produced in such a manner that a cross-finger type pattern of the comb-shaped opaque electrodes $1b$ and $1c$ is transferred by masking onto a substrate $1a$ made of glass or other transparent material by using photolithographing processing. The comb-shaped electrodes $1b$ and $1c$ are formed symmetrically by etching and chrome deposition, and these electrodes $1b$ and $1c$ are electrically isolated on the sample plate 1. For example, the electrodes $1b$ and $1c$ are arranged so that the width between each of the comb-shaped electrodes $1b$ and $1c$ is 100 $\mu$m, the width of the electrode itself is 20 $\mu$m, the formed electrode interval is 40 $\mu$m, and the grating pitch (P) produced by the formed electrode is 60 $\mu$. The size of the electrode area is greater than the illuminating laser beam diameter 10 mm$\phi$ and its shape is square having each side of approximately 12 mm. Then, in the direction parallel to the comb-shaped electrodes $1b$ and $1c$, the photoelectric element 5 is arranged with its longitudinal direction oriented therein.

On the other hand, a controller 6 is provided for the system control. The output of this controller 6 is connected to the semiconductor laser light source 2 through a laser driver 7. Also, the output of the controller 6 is directly connected to an amplifier 9 while it is also connected thereto through an alternating oscillator 8. The output from the amplifier 9 is connected to the respective comb-shaped electrodes 1b and 1c of the sample plate 1 so as to allow the alternating current voltage which varies periodically with the amplified voltage by the amplifier 9 to be applied to the comb-shaped electrodes 1b and 1c. Further, the output of the controller 6 is connected to the photoelectric element 5 through the CCD driver 10. The output of the photoelectric element 5 is connected to the controller 6 through a waveform treatment circuit 11 and A/D converter 12. Meanwhile, the output of the controller 6 is also connected to a ROM 17 and RAM 18 which are provided separately from ROM and RAM arranged in a display 13, keyboard 14, printer 15, disc memory 16, and controller 6.

In the present embodiment, latex particles of 1.0 $\mu m\phi$ are used as carrier particles to sensitize an immunoactive substance on the surface thereof, and an immunoactive substance is dispersed in a liquid medium having water as its main component to produce a reagent. A reaction solution prepared by mixing the test specimen and the reagent thus-produced. For the latex particles, those having the ionic character of either a cation or anion on the surface thereof are used. When this reaction solution is injected into the substrate 1a of the sample plate 1, the aggregating acceleration and measurement for a predetermined period of time are started by the operation of the keyboard 14. When the alternating current voltage is applied to the comb-shaped electrodes 1b and 1c, the ionic substances in the reaction solution, such as the latex particles having the ionic character on its surface and other ionic substances such as ions in the solution, are vibrated by the alternating current voltage applied across the electrodes 1b and 1c, titus accelerating the aggregation accordingly. Moreover, if only the alternating current voltage and its application time are made constant, the aggregation of the reaction solution can be conditioned substantially constant. It may be possible to apply any voltage if the voltage can be varied as the time elapses. A pulse voltage may be applied instead of the alternating voltage for example.

The light beam from the semiconductor laser light source 2 is irradiated on the sample plate 1 after having been converted into parallel rays of light by the collimator lens 3, and the transmitted beam forms an image on the photoelectric element 5 by the function of the lens 4. On the sample plate 1, a substantially periodic structure is formed by the opaque comb-shaped electrodes 1b and 1c, and the sample plate 1 is arranged on the front focusing plane of the lens 4 while the photoelectric element 5 is arranged on the rear side focusing plane thereof. It is therefore possible to obtain the spatial spectra of the sample plate 1 by the image formed on the photoelectric element 5.

Figure 3A:
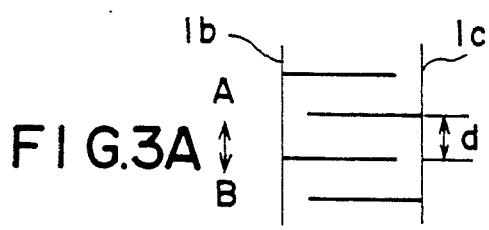
FIGS. 3A to 3H illustrate aggregated particle groups on the sample plate and spatial spectra.
Figure 3B:
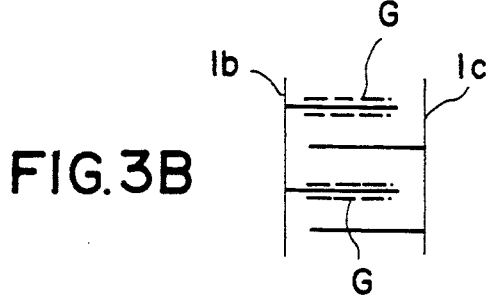
Figure 3C:
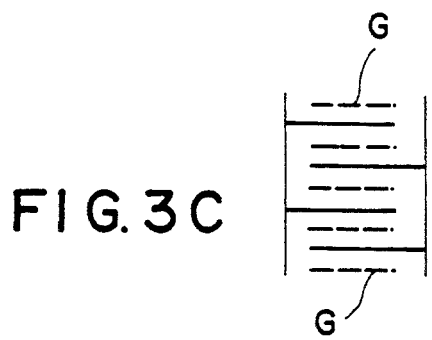
Figure 3D:
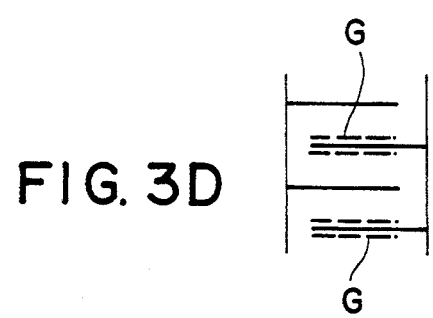
Figure 3E:
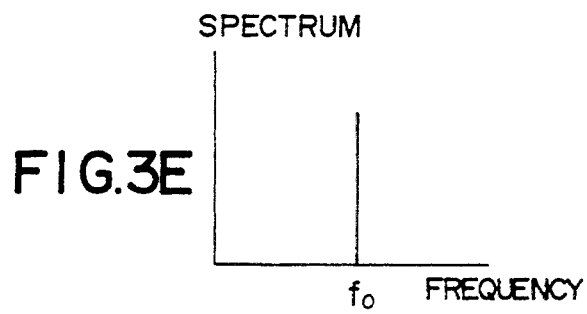

FIGS. 3A to 3H illustrate the states of the comb-shaped electrodes 1b and 1c of the sample plate 1 and the aggregated particle groups as well as the spatial spectra obtained from the photoelectric element 5. FIG. 3A shows the state of the comb-shaped electrodes 1b and 1c without any reaction solution being injected. In this case, the substantially periodic structure is formed only by the comb-shaped electrodes 1b and 1c, and as shown in FIG. 3E, the spatial spectrum on the photoelectric element 5 has only the basic frequency component fo corresponding to its grating pitch d. In practice, since the comb-shaped electrodes 1b and 1c present a rectangular amplitude grating, the higher harmonic wave component of the frequency fo is contained, though it is extremely slight. The duty of the grating, i.e., the width and interval of the electrodes, is not equal, thus allowing the higher harmonic wave component to produce a modulated spatial spectrum, but these effects are extremely small and negligible here. The description therefore is omitted.

When a test specimen is injected into this reagent on the sample plate 1, the state can be assumed to be as shown in FIGS. 3A and 3E because no aggregation occurs immediately after the injection of the test specimen. In practice, however, the carrier particles of approximately 1.0 $\mu m\phi$ are dispersed on the sample plate 1, which causes the laser beam to be scattered. As a result, on the spatial spectrum, a broad white low level noise is overlapped. In FIG. 3E, however, this noise is not shown.

Figure 3F:
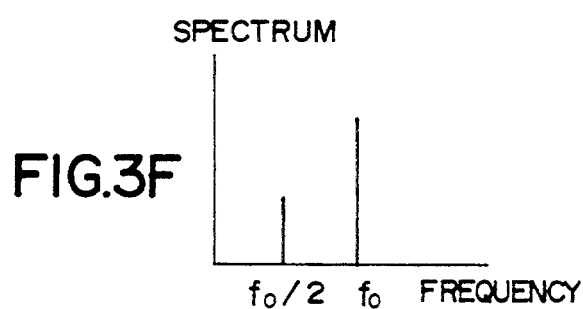

Subsequently, an alternating current field of zero-cross sinusoidal waves is generated across the comb-shaped electrodes 1b and 1c by an oscillator by a command from the controller 6 through the amplifier 9. Then, since the carrier particles are positively charged, the reaction solution L is caused to vibrate to accelerate the aggregation thereof. FIG. 3B illustrates the state where the aggregated particle group G is attracted to the comb-shaped electrode 1b by applying a negative voltage to the comb-shaped electrode 1b and a positive voltage to the comb-shaped electrode 1c after the acceleration of the aggregation by vibrating the reaction solution L for a predetermined period of time. In this state, since the opaque aggregation particle group G is uniformly attracted to the comb-shaped electrode 1b, its spatial spectrum becomes substantially the same as the case where the electrode width of the comb-shaped electrode 1b is made great. Accordingly, there appears a frequency component fo/2 corresponding to the electrode pitch 2d of the comb-shaped electrode 1b as shown in FIG. 3F.

Figure 3G:
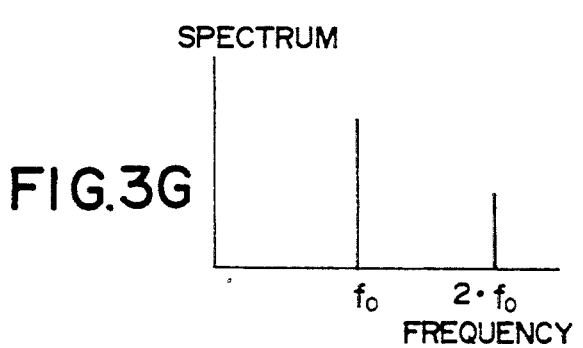

Now, from the state shown in FIG. 3B the applied voltage is gradually reduced to zero. Then, it can be assumed that the aggregation particle group G has been transferred to an intermediate position between the comb-shaped electrodes 1b and 1c and that a grating having a substantial grating pitch d/2 has been generated in addition to the frequency component fo shown in FIG. 3C. Then, the spatial spectrum at that time becomes as shown in FIG. 3G and the frequency component 2·fo corresponding to the grating pitch d/2 appears.

Figure 3H:
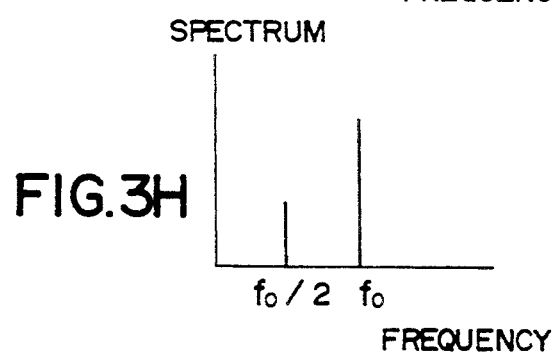

If a positive voltage is applied to the comb-shaped electrode 1b while a negative voltage is applied to the comb-shaped electrode 1c respectively, then the aggregation particle group G is attracted to the comb-shaped electrode 1c as shown in FIG. 3D. In this case, the phase of the diffracted light is different from the state shown in FIG. 3B, but the spatial spectrum becomes the same, thus enabling the frequency component fo/2 to appear as shown in FIG. 3H.

Thus, by applying an alternating current voltage to the comb-shaped electrodes 1b and 1c, the carrier particles can be vibrated electrically. Then, it is possible to obtain the spatial spectrum of the aggregation particle group G by controlling its position with the applied voltage to the comb-shaped electrodes 1b and 1c. Since the characteristics and amount of the immunoactive substance differentiate the size and amount of the aggregation particle group G to be created, it is possible to detect the presence of a desired immunoactive substance qualitatively or quantitatively by giving attention to the spatial spectrum, particularly of the level of the frequency components fo, fo/2, and 2·fo. In the actual detection, the comparisons with the reference data prepared in advance are executed, but when a calculation is made most simply, the data comparison can be executed using the varied portion of the spatial spectrum shown in FIG. 3E which can be of reference. If the spatial spectrum shown in FIG. 3E is subtracted from the spatial spectra measured in the states shown in FIGS. 3B through 3D, then the contribution of the aggregation particle group G to the spatial spectrum can be obtained.

Since the comb-shaped electrodes 1b and 1c of the sample plate 1 are substantially of the periodic structure in the A-B direction in FIG. 2, the spatial spectrum on the photoelectric element 5 is substantially axisymmetric in the A-B direction with respect to the optical axis. It suffices, therefore, if the photoelectric element 5 can detect a unidimensional spectrum distribution substantially on one side including the optical axis, and by reducing the numbers of the element, it becomes possible to read at higher speeds. Also, if the numbers of the element are small, the exposure time can be extended. Hence, the S/N ratio can be improved. Moreover, the resolution can be improved by making the size per element, i.e., the spatial sampling frequency of the spectrum distribution, smaller, thus, enabling the reduction of the fabrication cost.

Figure 4A:
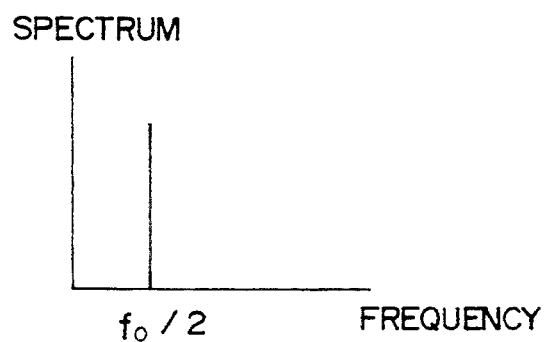
FIGS. 4A to 4C illustrate aggregated particle groups on the sample plate and spatial spectra.
Figure 4B:
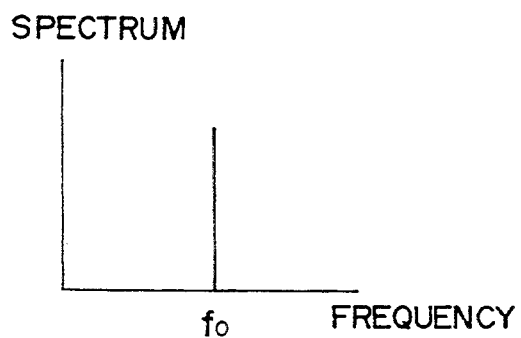
Figure 4C:
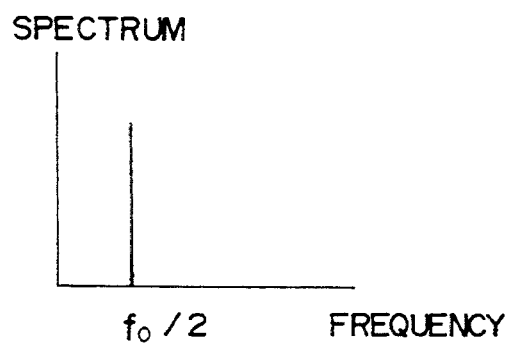

In the present embodiment, while the comb-shaped electrodes 1b and 1c are of the opaque chrome pattern, other metals such as gold or aluminum can be used instead. Then these become an optically high contrast amplitude-type grating. Also, it is possible to form the comb-shaped electrodes 1b and 1c with a transparent material such as ITO. In such a case, the component produced by the contribution of the comb-shaped electrodes 1b and 1c in the spatial spectrum can be removed. In other words, the states of the spatial spectrum shown in FIGS. 3B, 3C, and 3D become as shown in FIGS. 4A, 4B, and 4C respectively. Consequently, only the frequency component of the aggregation particle group G can be detected, thus making it possible to improve the S/N ratio and the detection accuracy as well.

In practice, since the refractive index of the glass substrate 1a of the sample plate 1 is approximately 1.5 and the refractive index of the ITO is approximately 1.9, the sample plate 1 becomes a phase-type grating including a phase difference proportional to the product of the difference between both the refractive indexes and the the thickness of the comb-shaped electrodes 1b and 1c when there is no reaction solution injected in the sample plate 1. Also, when the reaction solution is injected, the sample plate becomes a phase-type grating including a phase difference proportional to the product of the difference between the refractive indexes of both the reaction solution and the thickness of the comb-shaped electrodes 1b and 1c if there is any difference between the refractive indexes of the reaction solution and ITO. If the NA of a Fourier transform lens is great, the intensity of the spectrum of the phase grating is small, and there is no problem although it depends on the degree of the modulation of the phase. However, it is desirable to select a reaction solution medium which matches the refractive indexes of the transparent comb-shaped electrodes 1b and 1c in order to obtain sufficient effects of the present embodiment.

Now, the controlling method of the entire system will be described. In FIG. 1, when the measurement starting signal is inputted into the controller 6 by the operation of the keyboard 14, data are inputted into the controller 6 either from the keyboard 14, disk memory 16, ROM 17 or RAM 18, the data including a test specimen which is the object of the detection, granular diameter of the carrier particles as information of the carrier particles used, the optical characteristics such as charging condition, refraction factor, and absorption, a table carrying density, optimal alternating current frequency, voltage amplitude, application time, and the like, and the structure between the electrodes 1b and 1c, substrate material, resistance, capacitance, resonant frequency as information regarding the sample plate 1, and others. Then, the optimal measurement condition is determined from the data including these pieces of information. Then, on the basis of the frequency of the alternating current voltage associated with this measurement condition as well as the amplitude at the time of application, the controller 6 controls the oscillator 8 and amplifier 9 to apply the alternating voltage between the comb-shaped electrodes 1b and 1c while controlling the laser driver 7 to provide an optimal quantity of the laser light and further the CCD driver 10 to adjust the exposure time of the photoelectric element 5. The distribution of the spatial spectrum of the grating image projected on the photoelectric element 5 is converted into the time-series electric signals by the photoelectric element 5 being controlled by the CCD driver 10, and subsequent to the correction performed by the waveform treatment circuit 11, such signals are inputted into the controller 6 through the, A/D converter 12 to execute the qualitative and quantitative detection. The result thereof is output to the display 13, printer 15, disc memory 16, RAM 18, and the like. Here, it may be possible to receive the data from or transmit them to the outside by the use of a communicating function.

In the waveform treatment circuit 11, the sample hold, filtering, sensitivity correction of the photoelectric element 5 if required, dark output correction, shading correction of the optical system are executed for the output from the photoelectric element 5. It is preferable to make an arrangement so that the measurement can be repeated by modifying the quantity of the laser light from the semiconductor laser light source and the exposure time of the photoelectric element 5 as required after the data from the A/D converter 12 have been examined by the controller 6. Also, it may be possible to connect another D/A converter between the controller 6 and amplifier 9.

In this respect, as a measuring method, it is possible to measure time-changes and pseudo-transient responses by repeating the measurement at each time the time intervals of the vibration and aggregation are finely divided in addition to the measurement subsequent to the vibration given to the sample plate 1 for a predetermined period of time under specific conditions. This will be described later.

Figure 5:
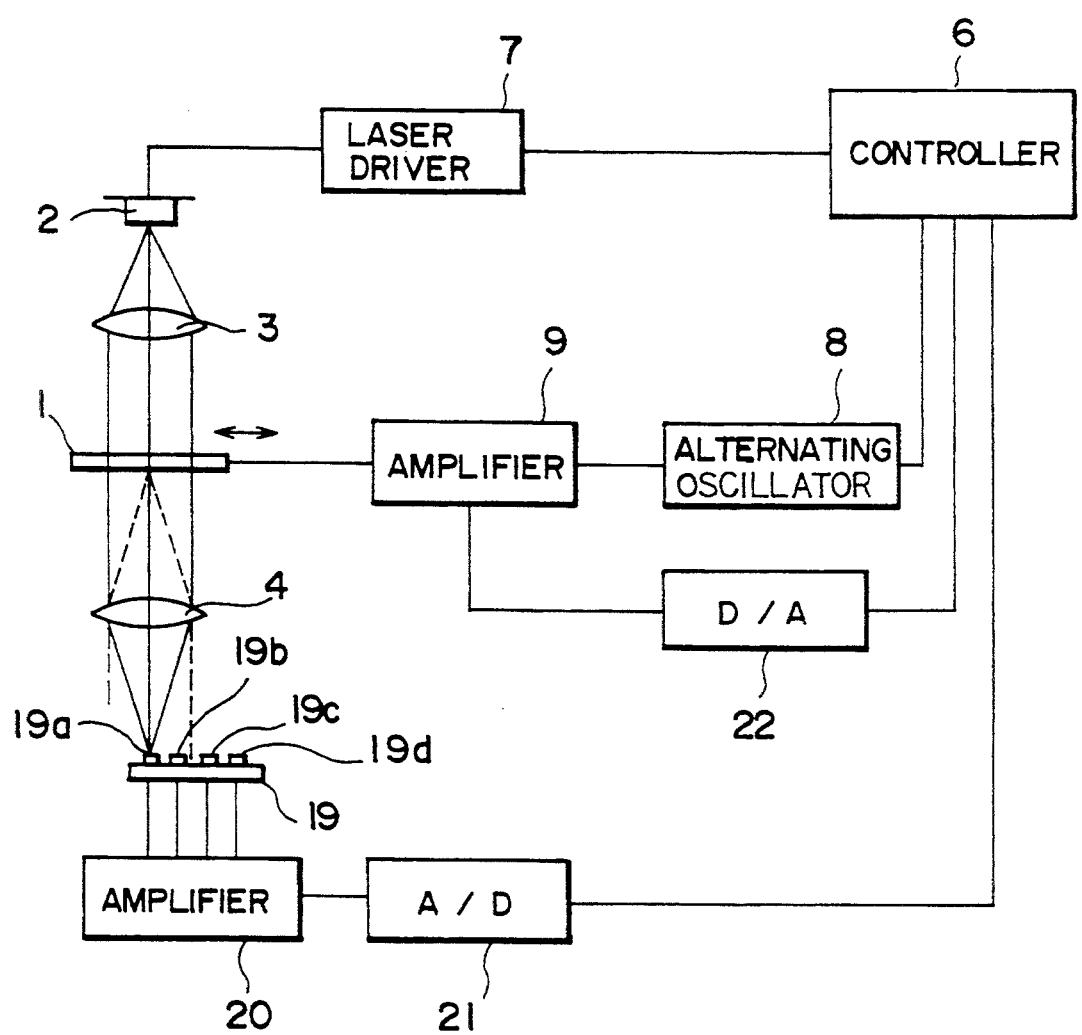
FIG. 5 is a diagram showing the structure of a second embodiment according to the present invention.

Now, FIG. 5 illustrates the principal structure of a second embodiment which is a modification of the above-mentioned embodiment. In FIG. 5, the same reference numerals as those appearing in FIG. 1 designate the same,, members.

In the present embodiment, a divisional sensor 19 in which sensor cells 19a through 19d comprising four divisional PIN photodiodes are packaged is arranged at the rear side focusing position of the lens 4 instead of the photoelectric element 5 used in the first embodiment. The output of the divisional sensor 19 is connected to an amplifier 20, and the output of the amplifier 20 is connected to an A/D converter 21. Then, the output of the A/D converter 21 is connected to a controller 6. Also, the output of the controller 6 is connected to an amplifier 9 through a D/A converter 22. The other structure arrangement is the same as the first embodiment and the representations thereof are not shown in FIG. 5.

The sensor 19a is arranged at a position to detect zero refraction light beam while each of the sensor cells 19b, 19c, and 19d is arranged at a position to detect each of the aforesaid frequency components $2 \cdot f_0$, $f_0$, and $f_0/2$, thus making it possible to detect only the luminous intensity of each frequency component efficiently. The current proportional to the luminous intensity output from the divisional sensor 19 is inputted into the controller 6 for the data processing through the A/D converter 21 after its current/voltage conversion, voltage amplitude, filtering, and the like have been performed by the amplifier 20.

In the present embodiment, while it is impossible to respond to the situation where the electrode pitches of the sample plate 1 are different or the spatial spectrum distribution varies due to the extremely different conditions of the aggregation, only the signal having the required frequency component can be detected efficiently. As a result, the structure of the apparatus and the signal processing become simpler. It may be possible to improve the selectivity of the detecting spectrum ranges by providing an aperture, pinhole, and the like in front of the divisional sensor 19 as required.

Now, in the above-mentioned embodiments, the aggregating conditions are constantly maintained by applying to the comb-shaped electrodes an alternating voltage having a specific state for a predetermined time of period. Then, an optical detection is conducted in a static state where a direct current voltage is being applied for detecting the aggregated conditions in an equilibrium state or semi-equilibrium state. In contrast, a third embodiment according to the present invention will be described hereunder, in which a test specimen measurement is performed dynamically by grasping the changes in the transient response of the aggregation. In this respect, the drawings used above are also used for reference.

In FIG. 1, the sinusoidal wave output of an alternating oscillator 8 is applied to the sample plate 1 through the amplifier 9 by command from the controller 6 in order to accelerate aggregation. In a state where the aggregating reaction is yet to begin immediately after the voltage application, the sample plate 1 presents the state as shown in FIG. 3A while the spatial spectrum being obtained from the photoelectric element 5 presents the state as shown in FIG. 3E. When the aggregating reaction begins to progress, the states shown respectively in FIGS. 3B, 3C, 3D and 3B appear for each of the phases $\pi/2$, $\pi$, $3\pi/2$, and $\pi$ of the sinusoidal wave. Here, since the optical density of the aggregation group G is increased as the time elapses, the peak value of the spatial spectrum (FIGS. 3F, 3G, 3H, and 3F) is progressively increased at each phase of the sinusoidal wave.

In order to grasp this change, the output from the photoelectric element 5 is drawn in synchronism with each phases of the sinusoidal wave of the alternating oscillator 8 in the present embodiment, or the output of the photoelectric element 5 which is synchronized with the phase of the sinusoidal wave is drawn by causing the light source 2 to emit pulse light at a desirable phase to be drawn in synchronism with the sinusoidal wave.

Then, by evaluating the data thus obtained, it is possible to measure the transient response of the aggregating reaction.

More specifically, it becomes possible to evaluate the inclination or inflection point of the transient response curve to be obtained by tracing timewise, for example, the peak of the frequency $2f_0$ in FIG. 3G showing the state of the spatial spectrum corresponding to the phase $3\pi/2$ of the sinusoidal wave, or to implement the improvement of the measuring accuracy of the test specimen on the basis of the shortened period of time for the test specimen measurement and transient response characteristics by making a simple threshold evaluation. Also, it may be possible to improve the reliability of the test specimen measurement by making a total judgment by evaluating the transient response of the spectrum in a plurality of the phase states of the sinusoidal wave. In this respect, if only the transient response of an identified spectrum should be evaluated, it is still possible to make such an evaluation with the structure of the test specimen measuring apparatus shown in FIG. 5.

So far the description has been made of the case where the frequency, amplitude, and the like of the sinusoidal wave alternating current voltage applied to the comb-shaped electrodes are constant, but the present invention is not limited to these conditions. In other words, it is highly desirable to make an arrangement so that the aggregating conditions are controlled by real time while changing or modulating the frequencies, phases and amplitudes of the sinusoidal wave voltage to be applied in accordance with the response characteristics. For example, if the aggregating reaction is found to be slower in its acceleration, then the aggregating reaction can be accelerated by increasing the amplitude and/or frequency of the applied voltage. On the contrary, if the measurement of the transient response characteristics is found difficult because of the aggregating reaction which is too fast, the situation can be corrected by reducing the amplitude and/or frequency of the applied voltage.

Also, if a plurality of test specimens should desirably be separated, it is effective to evaluate the difference of the transient response characteristics. In such a case, if the time-frequency responses against the voltage applied to the aggregation particle group G are different by the test specimens, it is possible to improve the measuring accuracy of the test specimen more by making the output of the alternating oscillator 8 repeated sweeping waveforms or making the plural frequencies overlapped alternating waveforms.

There are, of course, response delays with respect to the waveforms of the applied voltage resulting from the transfer of the test particle group G between the comb-shaped electrodes. However, it is possible to evaluate them by creating the state of a desired spatial spectrum by correcting the measurement synchronism. On the contrary, by adding such delays to the evaluation parameter as another transient response characteristic, it may even be possible to make the test specimen measurement more accurate.

With the test specimen measuring apparatus set forth above, the reaction solution mounted on the substrate can be vibrated by the alternating voltage applied to the comb-shaped electrodes to accelerate the aggregation. Thus, by regulating the applied voltage and application time constantly as predetermined, the aggregating conditions can be maintained invariably. Moreover, after the acceleration of the aggregation is completed or while the aggregation is being accelerated, the spatial spectrum created by the comb-shaped electrodes, on which reaction solution mounted, is detected thereby to detect by its changes the presence of the immunoactive substance in the test specimen by qualitatively or quantitatively. As a result, with a simple structure, it is possible to accelerate the aggregation arbitrarily by electrical control without any mechanical vibration as well as to shorten the inspection time. Also, by controlling the alternating voltage to be applied to the comb-shaped electrodes, it is possible to obtain the spatial spectrum optically in a state that the aggregation particle group G is arbitrarily positioned. There is an advantage, therefore, that the detection can be performed more accurately.

Subsequently, another embodiments according to the present invention will be described.

Figure 6:
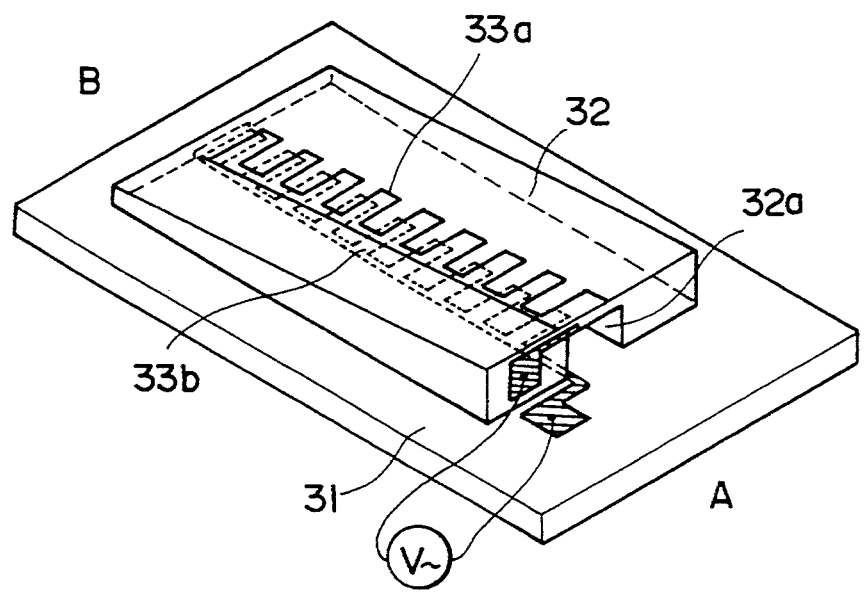
FIG. 6 is a perspective view illustrating a fourth embodiment according to the present invention.
Figure 7:
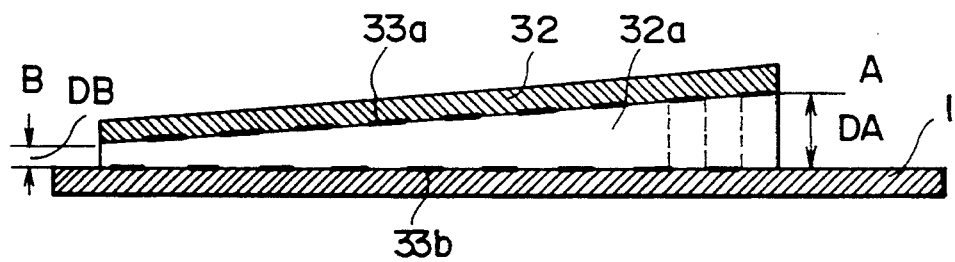
FIG. 7 is a vertical cross-sectional view of the fourth embodiment shown in FIG. 6.

FIG. 6 is a view showing the structure of a fourth embodiment according to the present invention. FIG. 7 is a vertically cross-sectional view in the direction A and B in FIG. 6. On a flat substrate 31 made of a transparent material, a wedge-shaped covering member 32, which is made of a transparent material with a concavity 32a arranged in the central inner side thereof, is closely provided, and a spatial portion is formed by the concavity 32a. As shown in FIG. 7, this concavity 32a is arranged so that the height of the space between the upper portion of the concavity 32a and the substrate 31 is gradually narrowed uniformly in the direction from A to B, and the vertical space DB at the end of the opening thereof is narrower than the diameter of the carrier particles to be used. The vertical space DA at the end of the opening in the A direction is wider than the vertical space DB by several times to approximately several hundred times so as to allow the aggregated particles to pass therethrough. Then, on the upper surface of the concavity 32a and the upper surface of the substrate 31 opposite thereto, comb-shaped electrodes 33a and 33b are formed respectively. Moreover, these comb-shaped electrodes 33a and 33b are arranged to face each other with deviation as shown in FIG. 7.

Figure 8:
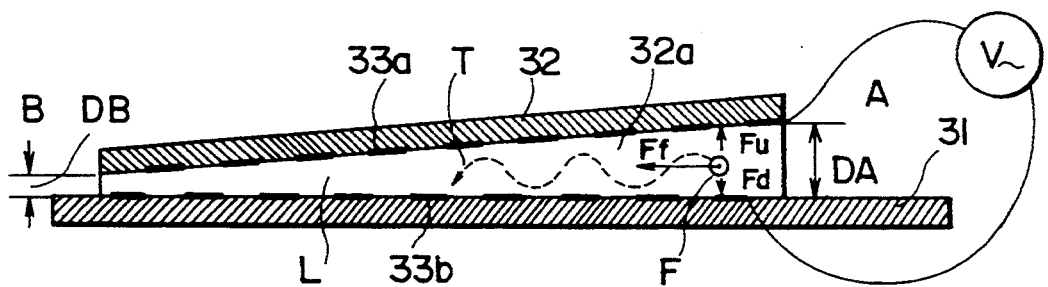
FIG. 8 is a view illustrating the measurement principle.
Figure 9:
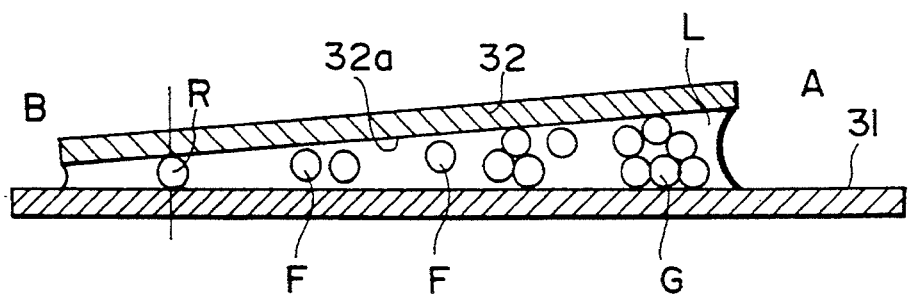
FIG. 9 is a view illustrating the measurement principle.
Figure 10:
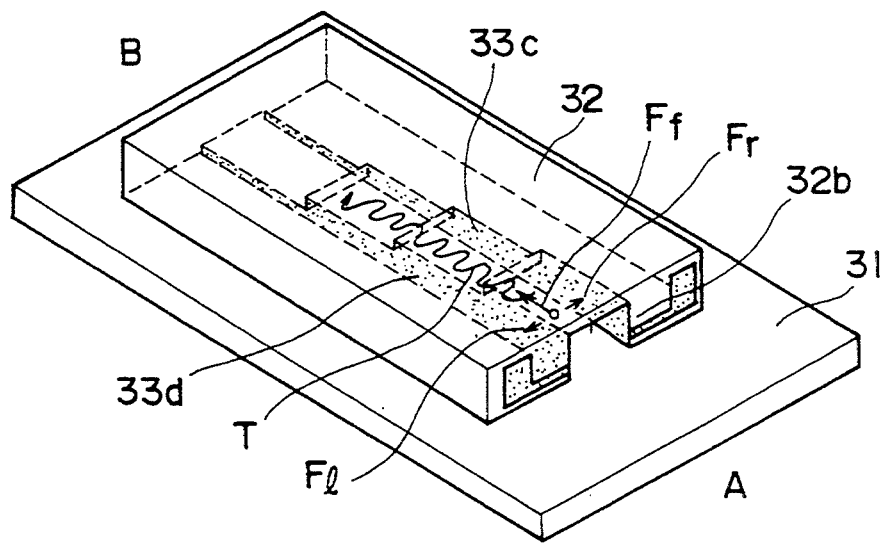
FIG. 10 is a view schematically illustrating a fifth embodiment according to the present invention.

Now, fluorescent carrier particles or colored carrier particles are prepared. Then, an immunoactive substance is sensitized to these particles. The particles thus prepared are mixed with a reagent and test specimen dispersed in a liquid medium having water as it main component to produce a mixture. When this mixture L is injected into the clearance between the substrate 32 and concavity 32a from the position A, the mixture L advances by surface tension in the direction B where the vertical space is getting narrower as shown in FIG. 8. By this surface tension, the carrier particles F are given a force toward the direction Ff. Also, in general, the immunoactive substance has a polar group when it is in a liquid medium. Therefore, this substance is affected by a force from an electric field. Likewise, the carrier particles F to which the immunoactive substance is sensitized are affected by a force from an electric field. However, it may be possible to given a polarity to the carrier particles F in advance.

When a time-changing voltage is applied to the comb-shaped electrodes 33a and 33b, a time-changing force Fd or Fu is given to the carrier particles F in response to the polarity of the electrode as shown in FIG. 8. As a result, the carrier particles F are immersed in the direction B with a locus represented by an arrow T. Likewise, the immunoactive substance in the test specimen, being given a force of the time-changing electric field, is immersed in the direction B with a waveform locus represented by an arrow T. However, this locus has different amplitude and frequency because the polarity or its intensity, mass and diameter thereof are different.

Therefore, the., agitation of the carrier particles F and test specimen is accelerated, and further at the same time of the aggregation being accelerated, the carrier particles F and aggregated matter are immersed in the direction B where the clearance is getting narrower. As shown in FIG. 9, the small diameter particles F can be carried further in the direction B, but the aggregated matter G is trapped on the way and cannot be carried any further depending on the size thereof.

The diameter of the aggregated matter G which is determined by the numbers of the carrier particles F which constitute one aggregated matter G, and the numbers of the aggregated matter G trapped by a certain clearance have a correlation with the characteristics and numbers of the immunoactive substance contained in the reaction liquid L, i.e., the aggregating state of the aggregated matter G created by the reaction. Consequently, with the reaction solution L flown into such clearance, it becomes possible for an examiner to discriminate and recognize with the naked eye easily the quantity of the carrier particles F trapped by the clearance R which is equal to the diameter R of the single carrier particles F as well as the position where the aggregated matter G is trapped. Thus, the qualitative and quantitative detection of the immunoactive substance can be conducted. In practice, the calibration curve is prepared in advance by the reaction solution L which has been reacted on a measuring test specimen containing the know immunoactive substance, and the detection is conducted by making comparison with such a calibration curve.

It may be possible to use an opaque material for either one of the substrate 31 and cover member 32. Also, it may be possible to devise means for an easy discrimination by forming either one of them with a black or gray material having a low lightness if the carrier particles F are among while group, for example. Also, in order to allow the reaction solution L to be immersed into the clearance easily, a material having a desirable affinity with the liquid medium for the reaction solution L can be coated on the inner surface of the clearance. Then, a more desirable result of the measurement is obtainable. For the coating material, it is preferable to use a hydrophilic substance, interfacial active agent, methylcellulose, carboxy methylcellulose, polyvinyl alcohol, polyacrylamide, or other water-soluble polymer if the liquid medium is water.

FIG. 10 is a view illustrating the structure of a fifth embodiment according to the present invention. On a flat substrate 31 made of a transparent material, a flat cover member 32 made of a transparent material with a concavity 32*b* arranged in the central inner side thereof is closely provided on the substrate 31 to form a clearance. This concavity 32*b* is arranged so that the height between the substrate 31 and concavity 32*b* is gradually shortened in four steps in the direction from A to B. The vertical space DB in the opening at the end portion in the B direction is smaller than the diameter of the carrier particles F while the vertical space DA in the opening at the end portion in the A direction is larger than the vertical space DB by several times to approximately several hundred times so as to allow the aggregated matter G to pass therethrough. Then, flat electrodes 33*c* and 33d are formed on the side portions of the concavity 32b to face each other.

In the present embodiment, also, the mixture L is injected from the position A, and when a time-changing voltage is applied to the electrodes 33c and 33d, a force Ff created by the surface tension and forces Fr and Fl are given by the time-changing polarities of the electrodes 33c and 33d to the carrier particles F and immunoactive substance in the test specimen as in the fourth embodiment. As a result, these particles and substance are caused to advance in the direction B with the locus represented by an arrow T so that the agitation and aggregation are accelerated. Then, the aggregated matter G is trapped on the way, and at the same time the distribution corresponding to each aggregation state is formed in the direction of the aforesaid electrodes in accordance with the voltage applied to the electrodes 3c and 33d as in the cases of the first embodiment and second embodiment. Likewise, the qualitative and moreover, quantitative detection of the immunoactive substance can be performed.

Figure 11:
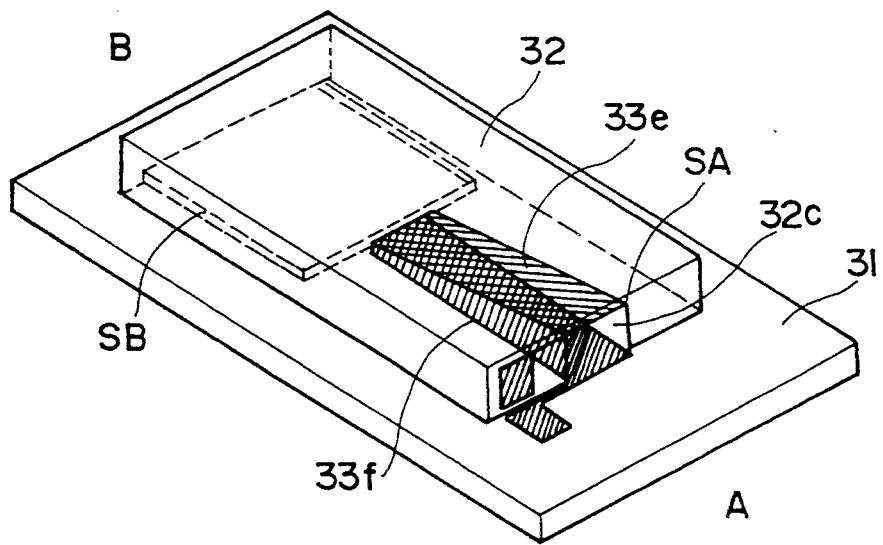
FIG. 11 is a view schematically illustrating a sixth embodiment according to the present invention.

FIG. 11 illustrates the structure of a sixth embodiment according to the present invention. On a flat substrate 31 made of a transparent material, a flat cover member 32 made of a transparent material with a concavity 32c arranged in the central inner side thereof is closely provided on the substrate 31 to form a clearance in the third embodiment. The vertical space of the clearance between the concavity 32c and substrate 31 is gradually narrowed uniformly in the direction from A to B, and from the position of the vertical space DB which is smaller than the diameter of the carrier particles F to be used, the width of the clearance is constant. Then, the volume of the clearance SB of the vertical space DB is made substantially equal to the volume of the clearance SA which has a larger vertical space than the vertical space DB or greater than that. In this respect, as in the fourth embodiment, the vertical space DA of the opening at the end portion in the direction A is larger than the vertical space DB by several times to several hundred times so as to allow the aggregated matter G to pass therethrough. On the upper plane of the concavity 32c and the upper surface of the substrate opposite thereto, the flat electrodes 33e and 33f are provided respectively and a time-changing voltage is applied to them.

In the present embodiment, also, when the mixture L is injected into the clearance between the substrate 31 and cover member 32 from the position A, the mixture L is caused by the surface tension to be immersed in the direction B where the vertical space is getting narrower while being given the force of the time-changing electric fields of the electrodes 33a and 33b. Accordingly, as in the fourth embodiment, the agitation and aggregation are accelerated. Then, the carrier particles F and aggregated matter G are trapped at the positions matching the respective diameters thereof. Hence, only the mixture of the liquid medium and test specimen is allowed to be transferred to the clearance SB of the vertical space DB. As the volume of this clearance SB is large, the major portion of the mixture which is not needed for detection is flown into this clearance, making it possible to detect only the trapped carrier particles F and aggregated matter G in the clearance SA of the larger vertical space more easily, thereby to obtain desirable measurement results.

In this respect, the shape of the vertical space DB is arbitrary as far as it satisfies the volume condition, and a liquid absorption member may also be provided in the clearance SB. Furthermore, it may be possible to define the vertical space DB slightly larger than the diameter of the carrier particles F within a limit of as much as approximately two times. In this case, the non-aggregated matter, i.e., the carrier particles F, are not trapped and absorbed into the clearance SB. Then, it becomes clearer and easier to discriminate the aggregated from the non-aggregated, hence making it possible to obtain better measurement results.

Figure 12:
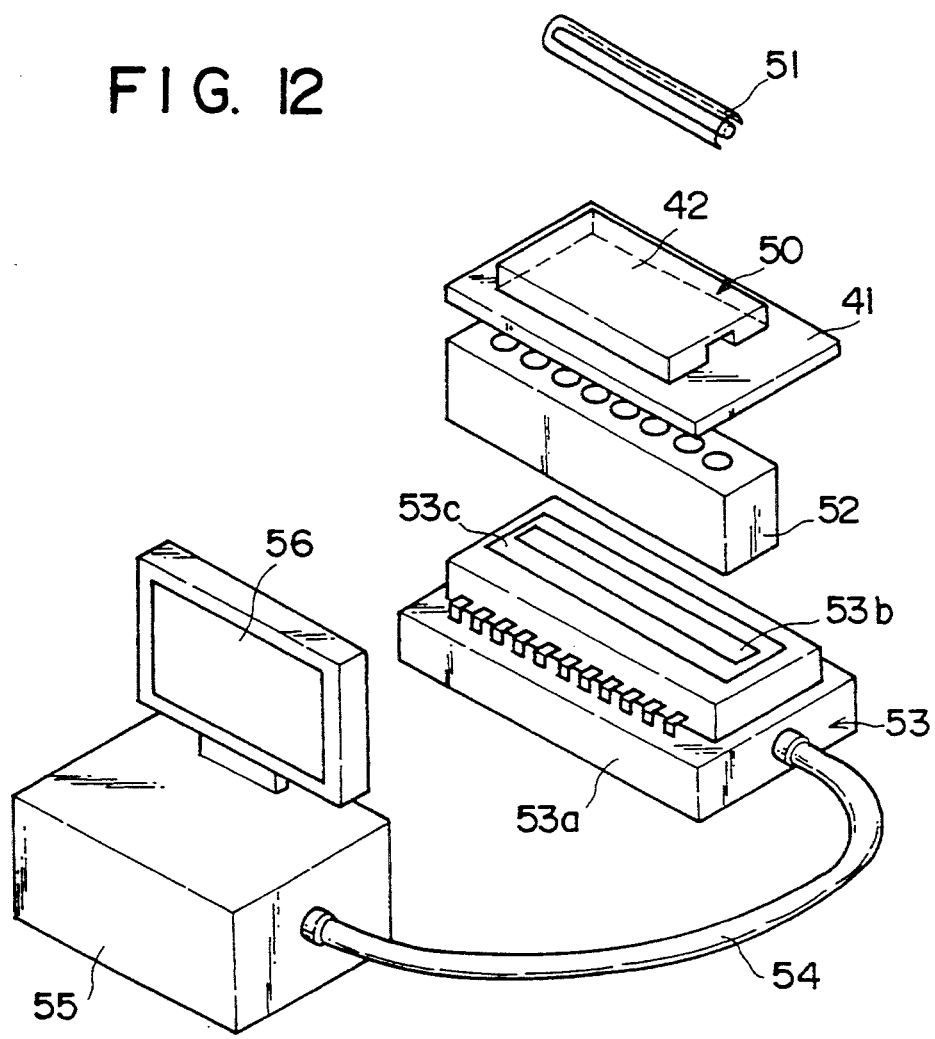
FIG. 12 is a view schematically illustrating a seventh embodiment according to the present invention.
Figure 13:
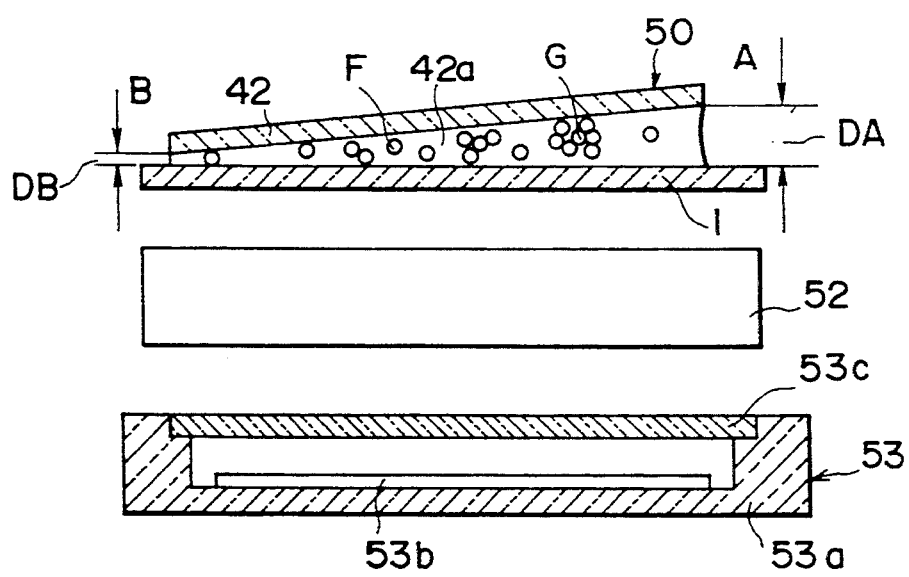
FIG. 13 is a cross-sectional view showing the optical system.

FIG. 12 illustrates the structure of a seventh embodiment according to the present invention in order that the states of the reaction solution may be read automatically. FIG. 13 is a cross-sectional view showing the optical system. The sample plate 50 used here is the same as the one in the fourth embodiment shown in FIG. 6.

In order to detect the fluorescing free particle F and others which are injected in the clearance arranged on the sample plate 50, a light source 51 is provided above the sample plate 50 to enable the fluorescent carrier particles to be excited through the band-pass filter and an image-formation optical system 52 comprising an image-formation lens, refraction factor contribution type lens, and the like is arranged below the sample plate 50. A light receiving optical system 53 is provided at a position where the image is formed. In the light receiving optical system 53, there is provided in the inner portion of the frame 53a a CCD array 53b having photosensitive elements of 14 $\mu$m $\times$ 14 $\mu$m (size) per element, which are arranged uni- or two-dimensionally, for example. This CCD array 53b is protected by a glass protection plate 53c mounted on the frame 53a. The output of each photosensitive element of the CCD array 53b is connected to the signal treatment unit 55 through a cable 54. The output of the signal treatment unit 55 is connected to a monitor 56.

Figure 14:
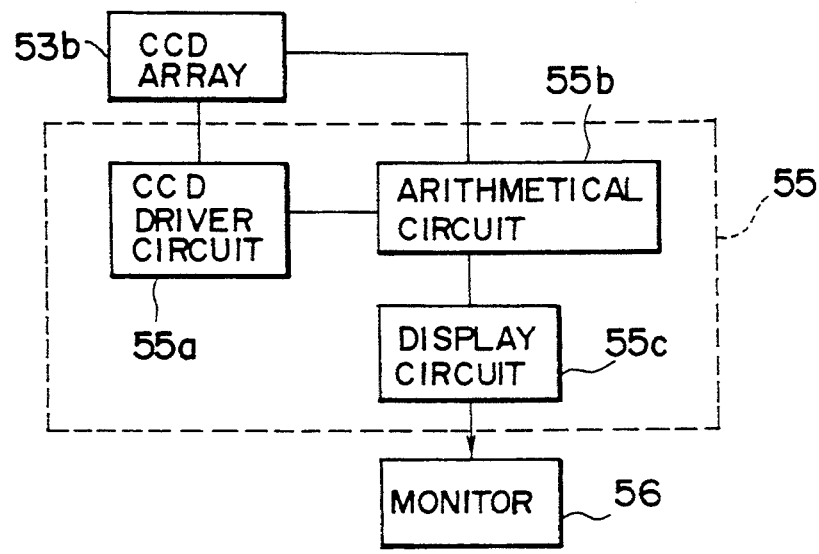
FIG. 14 is a diagram schematically showing the signal processing unit.

The inner structure of the signal treatment unit 55 is as shown in FIG. 14, and the output of the CCD array 53b is connected to the CCD driver circuit 55a and arithmetical circuit 55b. The output of the CCD driver circuit 55a is connected to the arithmetical circuit 55b. The output of the arithmetical circuit 55b is connected to a display circuit 55c. The output of the display circuit 55c is connected to the monitor 56.

Figure 15A:
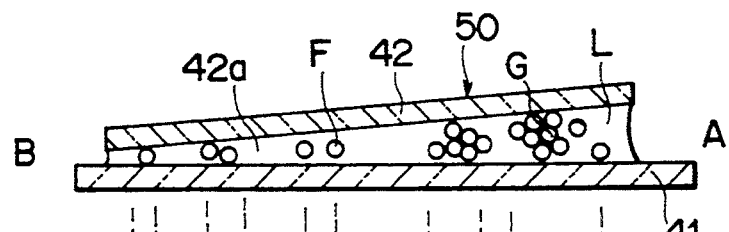
FIGS. 15A and 15B illustrate examples of obtainable signals.

An immunoactive substance such as a monoclonal antibody is sensitized to the fluorescent carrier particles F emitting fluoresce. When such carrier particles F are mixed with a reagent and test specimen dispersed in a liquid medium having water as its main component, a reaction occurs. Then, the plural numbers of the immunoactive substance and carrier particles F form an aggregated matter G. After a sufficient reaction, this reaction solution L is injected into the clearance between the substrate 41 and concavity 42a from the position A as shown in FIG. 15A. Then, as in the case of the aforesaid fourth embodiment, the agitation of the carrier particles F and test specimen is accelerated. Further, at the same time of the acceleration of the aggregation, the carrier particles F and its aggregated matter are immersed in the direction B into the narrower clearance. The particles F which have a smaller diameter can be transferred deeply in the direction B, but the aggregated matter G is trapped on the way due to its diameter and cannot be transferred any further.

At this juncture, the fluorescent image of the reaction solution L in the concavity 42a of the sample plate 10 is focused by the image-formation optical system 52 on the CCD array 53b of the light receiving optical system 53 and is converted photoelectrically by the CCD driver circuit 55a. Hence, the output voltage value of each photosensitive element is inputted into the arithmetical circuit 55b.

Figure 15B:
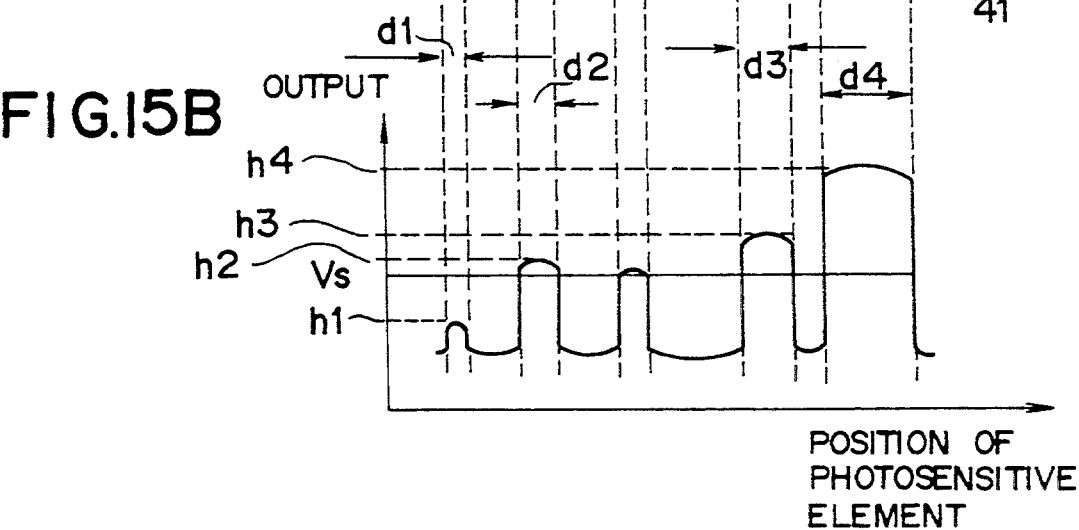

FIG. 15B shows the output voltages of each of the photosensitive elements corresponding to the image of the separated state represented in FIG. 15A. By the fluorescence emitted by the free particle F and aggregated matter G, the output voltages thereof become greater at the locations where the particle and matter are trapped. Thus, the presence thereof is detected accordingly.

In practice, a calibration curve is prepared in advance by the reaction solution L reacted to the measuring test specimen containing the known immunoactive substance, and the comparison is made therewith to make determination. As a calculation made by the arithmetical circuit 55b, the distribution of the maximal values of the output voltages h1, h2, h3, and h4 and the amplitudes d1, d2, d3, and d4 are compared with that of the calibration curve, or it may be possible to count simply the numbers of the photosensitive elements having the higher output voltage values than the threshold value Vs for comparison. The processing method thereof is not limitted to the abovementioned method. The results of the arithmetic processing are displayed on the monitor 56 through the display circuit 55c.

The test specimen measuring apparatus set forth above is provided with a clearance which is gradually narrowed with uniformity or steps from a maximal space which is sufficiently larger than the diameter of the carrier particles to a minimal space which smaller than the diameter of the carrier particles and is of a simple structure that electrodes are formed on the planes of the clearance which face each other. When a time-changing voltage is applied to the electrodes and a mixture is injected from the opening having the maximal space, the carrier particles and aggregated matter are agitated and aggregated by the electric field thus generated. Moreover, due to the differences in the space of the clearance, the carrier particles, aggregated matter, liquid medium, and the like, which are different in the sizes thereof are separated. Thus, from the transparent surface, the aggregating degree of the reaction solution can be discriminated and recognized clearly, and by comparing the calibration curve prepared in advance or the like means, it is possible to perform the qualitative or quantitative detection of the immunoactive substance in the test specimen highly precisely with a desirable producibility.

What is claimed is:

1. An apparatus for measuring a specified substance in a test specimen, comprising:
    receiving means for receiving a reaction solution of the test specimen and carrier particles which carry a substance specifically reacting to the specified substance in the test specimen, the reaction solution forming aggregating states of the carrier particles;
    comb-shaped electrodes to which variable voltage is applied, for forming a variable electric field in the reaction solution;
    means for optically detecting spatial spectrum distribution formed by said carrier particles around said comb-shaped electrodes; and
    means for determining the aggregating states of the carrier particles on the basis of the detected spatial spectrum distribution.

2. An apparatus according to claim 1, wherein said variable voltage is alternating voltage.

3. An apparatus according to claim 1, wherein said variable voltage is pulse voltage.

4. An apparatus according to claim 1, wherein said detecting means includes means for extracting a change of said spatial spectrum distribution.

5. An apparatus according to claim 1, wherein the substance specifically reacting to said specified substance includes an antibody or an antigen.

* * * * *